United States Patent [19]

Merianos

[11] Patent Number: 5,108,742
[45] Date of Patent: * Apr. 28, 1992

[54] ANHYDROUS COMPLEXES OF PVP AND $H_2O_2$

[75] Inventor: John J. Merianos, Middletown, N.J.

[73] Assignee: ISP Investments Inc., Wilmington, Del.

[*] Notice: The portion of the term of this patent subsequent to Apr. 16, 2008 has been disclaimed.

[21] Appl. No.: 581,353

[22] Filed: Sep. 12, 1990

Related U.S. Application Data

[62] Division of Ser. No. 434,943, Nov. 8, 1989, Pat. No. 5,008,093.

[51] Int. Cl.$^5$ .......................... A61K 3/79; C01B 15/01
[52] U.S. Cl. .................. 424/78.32; 424/401; 424/433; 424/443; 424/466; 424/616
[58] Field of Search .......................................... 424/80

[56] References Cited

U.S. PATENT DOCUMENTS 3,376,110 4/1968 Shiraeff ............................... 524/438
3,480,557 11/1969 Shiraeff ............................... 252/186

Primary Examiner—Thurman K. Page
Assistant Examiner—Peter F. Kulkosky
Attorney, Agent, or Firm—Walter Katz; Joshua J. Ward; Marilyn J. Maue

[57] ABSTRACT

What is provided herein are substantially anhydrous complexes of PVP and $H_2O_2$ in molar ratios of between about 2:1 and 1:1, respectively, which corresponds to between about 13% and about 23% by weight $H_2O_2$. The complexes of the invention are prepared by an anhydrous process whereby substantially uniform, free-flowing, fine white powders are obtained.

11 Claims, No Drawings

ANHYDROUS COMPLEXES OF PVP AND $H_2O_2$

This is a division of application Ser. No. 434,943, filed Nov. 8, 1989, now U.S. Pat. No. 5,008,093.

BACKGROUND OF THE INVENTION

1. Field of the Invention

This invention relates to substantially anhydrous complexes of polyvinylpyrrolidone (PVP) and hydrogen peroxide ($H_2O_2$), and to a process for preparing such stabilized complexes as free-flowing, uniform, fine white powders containing a predetermined amount of $H_2O_2$ therein.

2. Description of the Prior Art

Stabilized $H_2O_2$ compositions have found wide utility in commercial and industrial applications, e.g. as disinfectants, sterilization agents, as bleaching materials, washing concentrates, etchants, in cosmetic preparations, as clarification agents for alcoholic and fermented beverages, and as a catalyst in polymerizations requiring a free radical source. In biological applications which require a disinfectant or sterilization agent, such $H_2O_2$ compositions require release of an effective amount of oxygen at a controlled rate without storage decomposition caused by interaction with organic matter light and/or heat.

Shiraeff, in U.S. Pat. Nos. 3,376,110 and 3,480,557, discloses a solid, stabilized hydrogen peroxide composition of hydrogen peroxide and a polymeric N-vinyl heterocyclic compound prepared in an aqueous solution of the components. These compositions generally were prepared by mixing various weights of PVP and aqueous $H_2O_2$, and evaporating the solution to dryness. The Shiraeff composition, which was believed to be a solid, dry complex, was described as not necessarily anhydrous due to the hydrophilic nature of the PVP and the water present in the reaction solution. Shiraeff further stated that such amounts of water could be tolerated, however, if it did not affect the solid dry characteristics of the complexes. The $H_2O_2$ content of the composition was given as being at least 2%, and preferably 4.5 to 70% by weight. Prolonged drying to remove water from such compositions, however, resulted in loss of $H_2O_2$ forming a brittle, transparent, gummy, amorphous product. In U.S. Pat. No. 3,480,557, the aqueous PVP-$H_2O_2$ complexes, upon heating to dryness, produced hard, brittle chips which had a variable $H_2O_2$ content ranging from about 3.20 to 18.07% by weight, depending upon the drying times.

Drauz et al., in U.S. Pat. No. 4,564,514, disclosed a process for making water-free organic hydrogen peroxide solutions from aqueous solutions of hydrogen peroxide. The Drauz process effected removal of water by azeotropic distillation of water in high boiling organic solvents.

Accordingly, it is an object of this invention to provide substantially anhydrous complexes of PVP and $H_2O_2$.

Another object herein is to provide such anhydrous complexes of PVP and $H_2O_2$ in predetermined molar ratios of PVP to $H_2O_2$.

A particular object of the present invention is to provide stable, anhydrous complexes of PVP and $H_2O_2$ in a molar ratio of between about 2:1 and 1:1, respectively.

A further object of the invention is to provide a process of precipitating anhydrous complexes of PVP and $H_2O_2$ from an anhydrous organic solvent as a substantially uniform, free-flowing, fine white powder.

Still another object therein is to provide an anhydrous process of making a stabilized anhydrous PVP-$H_2O_2$ complex containing about 23% $H_2O_2$.

These and other objects and features of the invention will be made apparent from the following description.

SUMMARY OF THE INVENTION

What is provided herein are stabilized, substantially anhydrous complexes of PVP and $H_2O_2$ in a molar ratio of between about 2:1 and 1:1, respectively, which corresponds to between about 13% and about 23% by weight $H_2O_2$. The invention further includes an anhydrous process of preparing such complexes of PVP and $H_2O_2$ as a substantially uniform, free-flowing, fine white powder.

DETAILED DESCRIPTION OF THE INVENTION

In accordance with the invention, anhydrous PVP-$H_2O_2$ complexes are provided having a predetermined molar ratio of PVP to $H_2O_2$ ranging from between about 2:1 to about 1:1, corresponding to a $H_2O_2$ content of about 13% to about 23%. The anhydrous PVP-$H_2O_2$ complexes are prepared by an anhydrous process from a substantially anhydrous organic solvent and are obtained by filtration of the precipitate from suspension as a uniform, free-flowing, fine white powder.

The PVP polymeric starting material used in the present invention is available commercially as a solid of varying molecular weight, water solubility and water content. A typical PVP polymer is water soluble PVP-K30 (GAF Corp.) which contains less than 5% water. Other PVP polymers of different molecular weight, water solubility and water content also may be used, as for example, K-90 and K-120; Polyclar AT; Crospovidone; and the like. Both water soluble and water insoluble PVP polymers may be used.

In this process, the PVP powder is suspended in a suitable anhydrous organic solvent, such as a carboxylic acid ester, an alkyl ether, e.g. t-butyl methyl ether, or a hydrocarbon, e.g. cyclohexane. Preferably, however, an alkyl or cycloalkyl ester of a saturated aliphatic carboxylic acid is used, as for example, ethyl acetate, propyl acetate, isopropyl acetate, butyl acetate and ethyl propionate. The PVP suspension in ethyl acetate, for example, then is cooled, preferably to about 0° C., at which temperature precipitation of the desired complex as a fine powder may suitably occur.

An anhydrous $H_2O_2$ solution in an anhydrous organic solvent, preferably the same carboxylic acid ester used to form the PVP suspension, then is prepared according to the process of U.S. Pat. No. 4,564,514. In this step, an aqueous $H_2O_2$ solution (e.g. a 50% solution) is treated with the ester and then subjected to azeotropic distillation at a predetermined low pressure, e.g. at 200 mm Hg and 55° C. The resultant product is an anhydrous $H_2O_2$ solution in the ester having a $H_2O_2$ concentration in the range of about 20 to 50% $H_2O_2$.

Thereafter the thus-prepared anhydrous $H_2O_2$ solution is slowly added to the cooled PVP suspension in an anhydrous solvent in an amount corresponding to the desired molar ratio of PVP and $H_2O_2$. Preferably, however, a small excess of the $H_2O_2$ solution over the desired stoichiometric ratio is used. For example, to prepare a PVP-$H_2O_2$ complex with a 1:1 molar ratio, about 111 g. PVP and 100 g. of a 42% $H_2O_2$ and 300 ml of anhydrous solvent is used, providing a small excess, e.g. about 5%, over the required stoichiometric amount of 34 g. $H_2O_2$. This excess $H_2O_2$ is recoverable from the mother liquor.

Upon mixing the PVP and $H_2O_2$, a fine white powder is obtained which is filtered and dried at about 40°–50° C. in vacuo to remove residual solvent. The product is a stable, anhydrous complex in the form of a uniform, free-flowing, fine white powder having a $H_2O_2$ content between about 13% (2:1 molar ratio) and 23% $H_2O_2$ (1:1 molar ratio). The water content of the product generally is equal to or less than the amount present in the PVP starting material, and usually is less than 1%, preferably about 0.5%.

EXAMPLE 1

Preparation of Anhydrous 1:1 PVP-$H_2O_2$ Complex

PVP K-30 (GAF Corp.) (4.5% water), 111 g., was suspended in 200 ml. of anhydrous ethyl acetate (0.01% $H_2O$), and the suspension was cooled to 0° C. An anhydrous hydrogen peroxide solution in ethyl acetate was prepared by treating 200 g. of 50% aqueous hydrogen peroxide with 6 l. of ethyl acetate and azeotroping in a rotary evaporator to remove 100 g. of water. A 42.7% $H_2O_2$ solution in anhydrous ethyl acetate was obtained. Then 100 g. of this solution was added slowly over a period of about 1½ hours to the PVP suspension. A fine white precipitate formed which was filtered and dried in vacuo. The resultant water soluble complex contained 23.4% by weight $H_2O_2$ and 0.5% by weight water, upon drying at 50° C. in vacuo for 2 hours.

EXAMPLE 2

Preparation of Anhydrous 2:1 PVP-$H_2O_2$ Complex

The process of Example 1 was followed using 50 g. of the $H_2O_2$ solution in anhydrous ethyl acetate. The resultant complex contained 13.2% $H_2O_2$ and 0.5% water.

EXAMPLE 3

200 g. of PVP-CI (K-30) was suspended in 300 g. of anhydrous ethyl acetate. Then $H_2O_2$, 424 g., 19.6% $H_2O_2$ and 0.84% $H_2O$ was added slowly to the cooled (5° C.) suspension of PVP/ethyl acetate. The addition required 45 minutes. The suspension then was stirred for another 45 minutes, filtered, and washed with anhydrous ethyl acetate. The fine powder was dried at 40°–50° C. for 2 hours under vacuum to recover ethyl acetate. The yield was 258.8 g. of water soluble PVP-$H_2O_2$ containing 23.1% $H_2O_2$ and 0.4% $H_2O$ as a free flowing white powder. The mother liquor of ethyl acetate, 485 g. contained 4.51% $H_2O_2$.

EXAMPLE 4

35 g. of crospovidone was suspended in 100 ml. of anhydrous ethyl acetate. Then $H_2O_2$, 27.5 g., as a 42.7% $H_2O_2$ solution was added with cooling at 5°–10° C. The mixture was stirred for 1 hour. The precipitated complex was filtered to provide 46.1 g. of a water insoluble PVP-$H_2O_2$ complex containing 24.9% $H_2O_2$, after drying at 40°–50° C. for 2 hours.

COMPARATIVE EXAMPLE

Preparation of Aqueous PVP-$H_2O_2$ Complex According to U.S. Pat. No. 3,480,557

6 g. of PVP-CI (K-30) (GAF Corp.) (4.5% water) was dissolved in 50 ml. of methanol. Then 7 g. of a solution of $H_2O_2$ in water (50%) was added, followed by heating at 45° C. for 2 hours, and evaporation of methanol for 12 hours. A gummy, amorphous residue contained 12.92% $H_2O_2$ and 5% $H_2O$.

EXAMPLE 5

Stability of Anhydrous Complex of Example 1

After 43 days at 60° C. the complex lost only 15% of its $H_2O_2$ activity, which shows excellent stability toward decomposition. At room temperature, decomposition was only 1.5% after 60 days.

It is to be understood that the above examples are provided to illustrate specific and preferred embodiments of the invention and that many modifications and alterations can be made in these examples without departing from the scope of the invention.

What is claimed is:

1. An anhydrous process of preparing stable, uniform, free-flowing, fine white powders of an anhydrous complex of PVP and $H_2O_2$ having a molar ratio of PVP to $H_2O_2$ between about 2:1 and about 1:1, respectively comprising reacting PVP in suspended form in an anhydrous organic solvent and $H_2O_2$ in substantially the same molar ratio of reactants as predetermined for the complex, the water content of the complex being equal to or less than the amount of water present in the PVP starting material, and substantially no free hydrogen peroxide being present therein.

2. An anhydrous process according to claim 1 wherein said reaction is carried out at a temperature which is below room temperature.

3. An anhydrous process according to claim 2 wherein said temperature is about 0° to about 5° C.

4. An anhydrous process according to claim 1 wherein said anhydrous organic solvent is an ester or ether.

5. An anhydrous process according to claim 4 in which said solvent is anhydrous ethyl acetate.

6. An anhydrous process according to claim 1 wherein said PVP and $H_2O_2$ are reacted in a slight excess of $H_2O_2$ over a 1:1 molar ratio of PVP to $H_2O_2$.

7. An anhydrous process according to claim 1 wherein said reaction is carried out by slowly adding a solution of $H_2O_2$ in an anhydrous organic solvent to a suspension of PVP in an anhydrous organic solvent.

8. An anhydrous process according to claim 1 wherein a slight excess of $H_2O_2$ over a 2:1 molar ratio of PVP to $H_2O_2$ is used.

9. An anhydrous process according to claim 1 wherein the complex has a water content of less than 1% by weight.

10. A method according to claim 1 in which the molar ratio of the complex is about 2:1.

11. A method according to claim 1 in which the molar ratio of the complex is about 1:1.

* * * * *